US008740869B2

(12) United States Patent
Velazquez et al.

(10) Patent No.: US 8,740,869 B2
(45) Date of Patent: Jun. 3, 2014

(54) PERSONAL CARE ARTICLES WITH TACTILE VISUAL CUES (75) Inventors: Herb Velazquez, Neenah, WI (US); Tom Flicker, Minneapolis, MN (US); Duane McDonald, Neenah, WI (US); Suzanne Murray, Appleton, WI (US); Katherine C. Wheeler, Menasha, WI (US); Dean M. Wydeven, Appleton, WI (US); Lisha Yu, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 364 days.

(21) Appl. No.: 13/046,135

(22) Filed: Mar. 11, 2011

(65) Prior Publication Data

US 2012/0232511 A1 Sep. 13, 2012

(51) Int. Cl.
A61F 13/49 (2006.01)

(52) U.S. Cl.
USPC .................................. 604/385.01

(58) Field of Classification Search
USPC .......................... 604/372, 385.01
See application file for complete search history.

(56) References Cited

U.S. PATENT DOCUMENTS

| | | | |
|---|---|---|---|
| 3,854,978 A | 12/1974 | Campbell, Sr. et al. | |
| 3,930,090 A | 12/1975 | Campbell, Sr. et al. | |
| 4,200,103 A | 4/1980 | Black et al. | |
| 4,285,746 A * | 8/1981 | DePuy et al. | 156/79 |
| 4,526,825 A | 7/1985 | Whitehead | |
| 4,834,739 A * | 5/1989 | Linker et al. | 604/385.04 |
| 4,845,778 A * | 7/1989 | Peterson | 2/24 |
| 4,850,991 A * | 7/1989 | Nakanishi et al. | 604/387 |
| 5,338,766 A | 8/1994 | Phan et al. | |
| 5,578,025 A | 11/1996 | May | |
| 5,624,423 A | 4/1997 | Anjur et al. | |
| 5,653,166 A * | 8/1997 | Mohammed et al. | 101/32 |
| 5,795,921 A | 8/1998 | Dyer et al. | |
| 5,807,367 A | 9/1998 | Dilnik et al. | |
| 6,015,454 A | 1/2000 | Lacroix et al. | |
| 6,040,494 A | 3/2000 | Kalentun et al. | |
| 6,140,551 A * | 10/2000 | Niemeyer et al. | 604/367 |
| 6,297,424 B1 * | 10/2001 | Olson et al. | 604/361 |
| 6,416,502 B1 | 7/2002 | Connelly et al. | |

(Continued)

FOREIGN PATENT DOCUMENTS

CN 201064524 Y 5/2008
EP 0 941 727 A1 9/1999

(Continued)

OTHER PUBLICATIONS

Wilflex Nupuff Base 10250NPF product sheet, Mar. 22, 2001.*

(Continued)

*Primary Examiner* — Susan Su
(74) *Attorney, Agent, or Firm* — Kimberly-Clark Worldwide, Inc.

(57) ABSTRACT

An absorbent article, for example, a diaper, a training pant, a swimming pant, or a feminine care article, and so forth, includes a topsheet, which forms a body-facing surface of the absorbent article, a backsheet disposed distally from the topsheet, which forms a garment-facing surface of the absorbent article, an absorbent core positioned between the topsheet and the backsheet, and a heat-activatable expandable treatment on the garment-facing surface. The heat-activatable expandable treatment is present on the garment-facing surface in a visually distinctive shape or pattern and provides visual and/or tactile cues to a user of the absorbent article.

26 Claims, 2 Drawing Sheets

(56) References Cited

U.S. PATENT DOCUMENTS

| | | | |
|---|---|---|---|
| 6,558,499 B1 * | 5/2003 | Pargass et al. | 156/250 |
| 6,569,136 B1 * | 5/2003 | Tao et al. | 604/385.01 |
| 6,592,562 B2 | 7/2003 | Menard et al. | |
| 6,626,879 B1 | 9/2003 | Ashton et al. | |
| 6,645,330 B2 * | 11/2003 | Pargass et al. | 156/73.1 |
| 6,737,114 B2 * | 5/2004 | Dawson et al. | 427/282 |
| 6,827,806 B2 | 12/2004 | Uitenbroek et al. | |
| 6,840,614 B2 * | 1/2005 | Wagner et al. | 347/101 |
| 6,852,905 B2 | 2/2005 | Baker | |
| 6,936,648 B2 | 8/2005 | Bagwell et al. | |
| 6,958,430 B1 | 10/2005 | Marinelli | |
| 7,247,674 B2 | 7/2007 | Kitano et al. | |
| 8,216,200 B2 * | 7/2012 | Meetz et al. | 604/385.13 |
| 2003/0120237 A1 | 6/2003 | Guidotti | |
| 2004/0172772 A1 * | 9/2004 | Santiago | 8/471 |
| 2005/0152624 A1 * | 7/2005 | Versluys | 383/107 |
| 2005/0182194 A1 | 8/2005 | He et al. | |
| 2005/0257881 A1 * | 11/2005 | Coose et al. | 156/256 |
| 2006/0018953 A1 | 1/2006 | Guillon et al. | |
| 2006/0135925 A1 * | 6/2006 | Hurley et al. | 604/385.01 |
| 2007/0049884 A1 * | 3/2007 | Long et al. | 604/361 |
| 2007/0098962 A1 * | 5/2007 | Laprade | 428/195.1 |
| 2008/0145532 A1 * | 6/2008 | McDonald | 427/244 |
| 2008/0208151 A1 | 8/2008 | Zacharias et al. | |
| 2009/0192482 A1 | 7/2009 | Dodge, II et al. | |
| 2009/0271914 A1 | 11/2009 | Bauer | |
| 2009/0294045 A1 * | 12/2009 | Marino et al. | 156/267 |
| 2009/0326409 A1 | 12/2009 | Cohen et al. | |
| 2010/0000897 A1 * | 1/2010 | Bumpass et al. | 206/440 |
| 2010/0164733 A1 * | 7/2010 | Ales et al. | 340/604 |
| 2010/0173119 A1 | 7/2010 | Vitarana et al. | |
| 2010/0179500 A1 * | 7/2010 | Roe et al. | 604/385.14 |
| 2010/0209521 A1 | 8/2010 | Schalkhammer | |
| 2010/0274213 A1 | 10/2010 | Gustin Bergstrom et al. | |
| 2011/0213325 A1 * | 9/2011 | Gabrielii et al. | 604/385.3 |
| 2012/0141698 A1 * | 6/2012 | OLeary et al. | 428/32.77 |
| 2012/0157949 A1 * | 6/2012 | Knight et al. | 604/361 |

FOREIGN PATENT DOCUMENTS

| | | | | |
|---|---|---|---|---|
| EP | 1 917 940 A2 | 5/2008 | | |
| EP | 2250982 A1 | 11/2010 | | |
| WO | WO 98/13003 A1 | 4/1998 | | |
| WO | WO 01/00117 A2 | 1/2001 | | |
| WO | WO 2006/071211 A1 | 7/2006 | | |
| WO | WO 2007/024327 A1 | 3/2007 | | |
| WO | WO 2010/070503 A2 | 6/2010 | | |
| WO | WO 2010/072388 A2 | 7/2010 | | |
| WO | WO 2010/076679 A2 | 7/2010 | | |
| WO | WO 2012082027 A1 * | 6/2012 | | A61F 13/56 |

OTHER PUBLICATIONS

U.S. Appl. No. 12/971,741, filed Dec. 17, 2010, by Poruthoor et al. for "Article With Heat-Activatable Expandable Structures.".

* cited by examiner

PERSONAL CARE ARTICLES WITH TACTILE VISUAL CUES

BACKGROUND OF THE INVENTION

Typical disposable personal care absorbent garments may include a liquid-permeable body-side liner, an absorbent core, and a liquid-impermeable garment-facing backing material. Surface properties and appearance of the components of the absorbent garments play an important role in having the components both function well and be aesthetically pleasing. Visual cues on the surface of absorbent products are known. For example, waist bands may be printed on a surface of an absorbent product to give the appearance that a waist band is present. However, visual cues can be missed if for some reason a user or caregiver is blocked from seeing a product well during the process of handling and donning the product. Accordingly, there is a need to improve the effectiveness of visual cues provided on the surfaces of absorbent personal care products.

SUMMARY OF THE INVENTION

Objects and advantages of the invention will be set forth in part in the following description, or may be obvious from the description, or may be learned through practice of the invention.

In one embodiment, an absorbent article, for example, a diaper, a training pant, a swimming pant, or a feminine care article, and so forth, includes a topsheet, which forms a body-facing surface of the absorbent article, a backsheet disposed distally from the topsheet, which forms a garment-facing surface of the absorbent article, an absorbent core positioned between the topsheet and the backsheet, and a heat-activatable expandable treatment on the garment-facing surface. The garment-facing surface may be the surface of a nonwoven material. The nonwoven material may, for example, be selected from the group consisting of film/nonwoven laminates, stretch-thinned laminates, stretch-bonded laminates and neck-bonded laminates. In one aspect, the garment-facing surface may have a first color and the heat-activatable expandable treatment may have a second color different than the first color.

In one aspect, the heat-activatable expandable treatment may have a thickness above the garment-facing surface of between about 0.2 and about 6 millimeters. Suitably, the heat-activatable expandable treatment may include a heat-activatable expandable ink. The heat-activatable expandable treatment may further include activated carbon particles. In another aspect, the heat-activatable expandable treatment or ink may include an elastomeric polymer.

In a further aspect, the heat-activatable expandable treatment may be present on the garment-facing surface in a visually distinctive shape or pattern. As one example, the visually distinctive shape or pattern may be in the area of a waistband or fastener. As another example, the visually distinctive shape or pattern may be a series of spaced lines, the lines spaced substantially in a stretch direction of the backsheet. The stretch direction of the backsheet may correspond to a lateral direction of the backsheet. As a further example, the heat-activatable expandable treatment may be on the garment-facing surface in a visually distinctive shape or pattern indicating where the garment-facing surface should be grasped during donning of the article. As an even further example, the heat-activatable expandable treatment may be on a rear waist region of the absorbent article and in a shape of a product label.

In another embodiment, a method of preparing an absorbent article includes the steps of:

providing an absorbent article including a topsheet which forms a body-facing surface of the absorbent article, a backsheet disposed distally from the topsheet which forms a garment-facing surface of the absorbent article, and an absorbent core positioned between the topsheet and the backsheet;

applying a heat-activatable expandable treatment onto the garment-facing surface; and, heating the heat-activatable expandable treatment to expand the heat-activatable expandable treatment.

The heat-activatable expandable treatment may have a thickness of greater than about 0.2 and about 6 millimeters after the heating step. The heat-activatable expandable treatment of the method may include a heat-activatable expandable ink. The backsheet in the absorbent article may include a nonwoven material. In one aspect, the garment-facing surface of the absorbent article may have a first color and the heat-activatable expandable treatment may have a second color different than the first color.

In one aspect, the applying step includes printing the heat activatable expandable treatment onto the garment-facing surface.

In another aspect, the heating step includes heating the heat-activatable expandable treatment to a temperature greater than about 100 degrees Fahrenheit.

In a further aspect, the heat-activatable expandable treatment may be applied to the garment-facing surface in a visually distinctive shape or pattern. As one example, the visually distinctive shape or pattern may be applied in the area of a waistband or fastener. As another example, the visually distinctive shape or pattern may be applied as a series of spaced lines in a waist region of the absorbent article, the lines spaced substantially in a stretch direction of the waist region. The stretch direction of the waist region may correspond to a lateral direction of the backsheet. As a further example, the heat-activatable expandable treatment may be applied on the garment-facing surface in a visually distinctive shape or pattern indicating where the garment-facing surface should be grasped during donning of the article. As an even further example, the heat-activatable expandable treatment may be applied on a rear waist region of the absorbent article and in a shape of a product label.

In an even further aspect, the heat-activatable expandable treatment may be applied to the garment-facing surface either before or after assembly of the absorbent article. Moreover, the heating step may occur either before or after assembly of the absorbent article.

Other features and aspects of the present invention are discussed in greater detail below.

BRIEF DESCRIPTION OF THE FIGURES

A full and enabling disclosure of the present invention, including the best mode thereof to one skilled in the art, is set forth more particularly in the remainder of the specification, which includes reference to the accompanying figures, in which.

Repeat use of reference characters in the present specification and drawings is intended to represent the same or analogous features or elements of the present invention.

DEFINITIONS

Within the context of this specification, each term or phrase below includes the following meaning or meanings.

As used herein the term "nonwoven fabric or web" refers to a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, coform processes, etc.

As used herein, the terms "meltblown web" or "meltblowing process" and variations thereof generally refer to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" and variations thereof generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

DETAILED DESCRIPTION OF REPRESENTATIVE EMBODIMENTS

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

The present invention relates generally to absorbent articles intended for personal wear, and more particularly to such absorbent articles having tactile visual cues on an outer surface of the absorbent articles.

An "absorbent article" generally refers to any article capable of absorbing water or other fluids. While one embodiment of an absorbent article of the present invention is described below in the form of a diaper, it is understood that the present invention is suitable for use with other absorbent articles intended for personal wear, including, but not limited to, personal care absorbent articles, such as diapers, training pants, absorbent underpants, incontinence articles, feminine hygiene products (e.g., sanitary napkins), swim wear, and so forth; medical absorbent articles, such as garments, fenestration materials, underpads, bedpads, bandages, absorbent drapes, and so forth; and other personal care or health care garments, and the like. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

Figure 1:
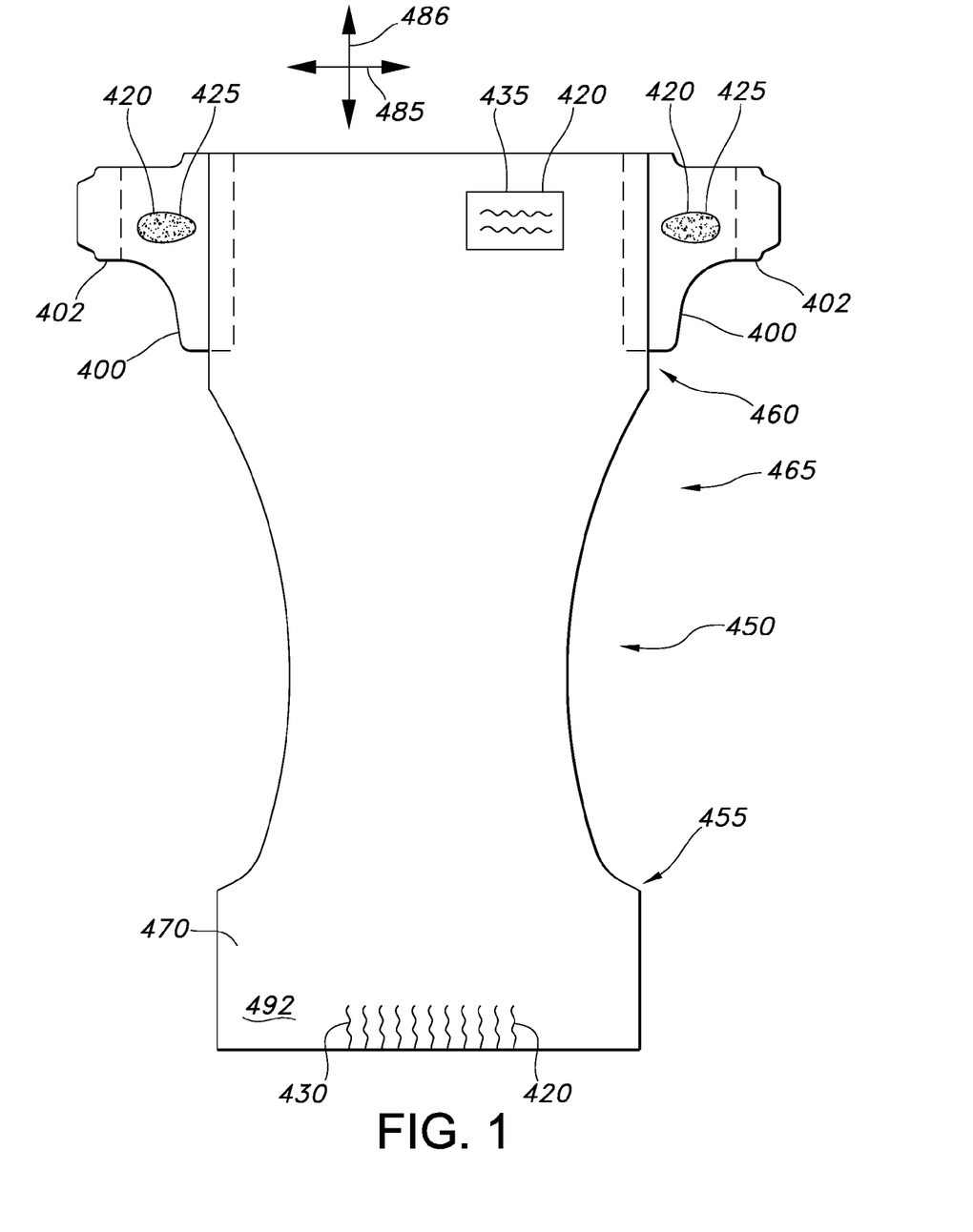
FIG. 1 is a top plan view of one embodiment of a personal care product of the present invention in a laid flat condition, and showing the surface of the personal care product that faces away from the wearer.
Figure 2:
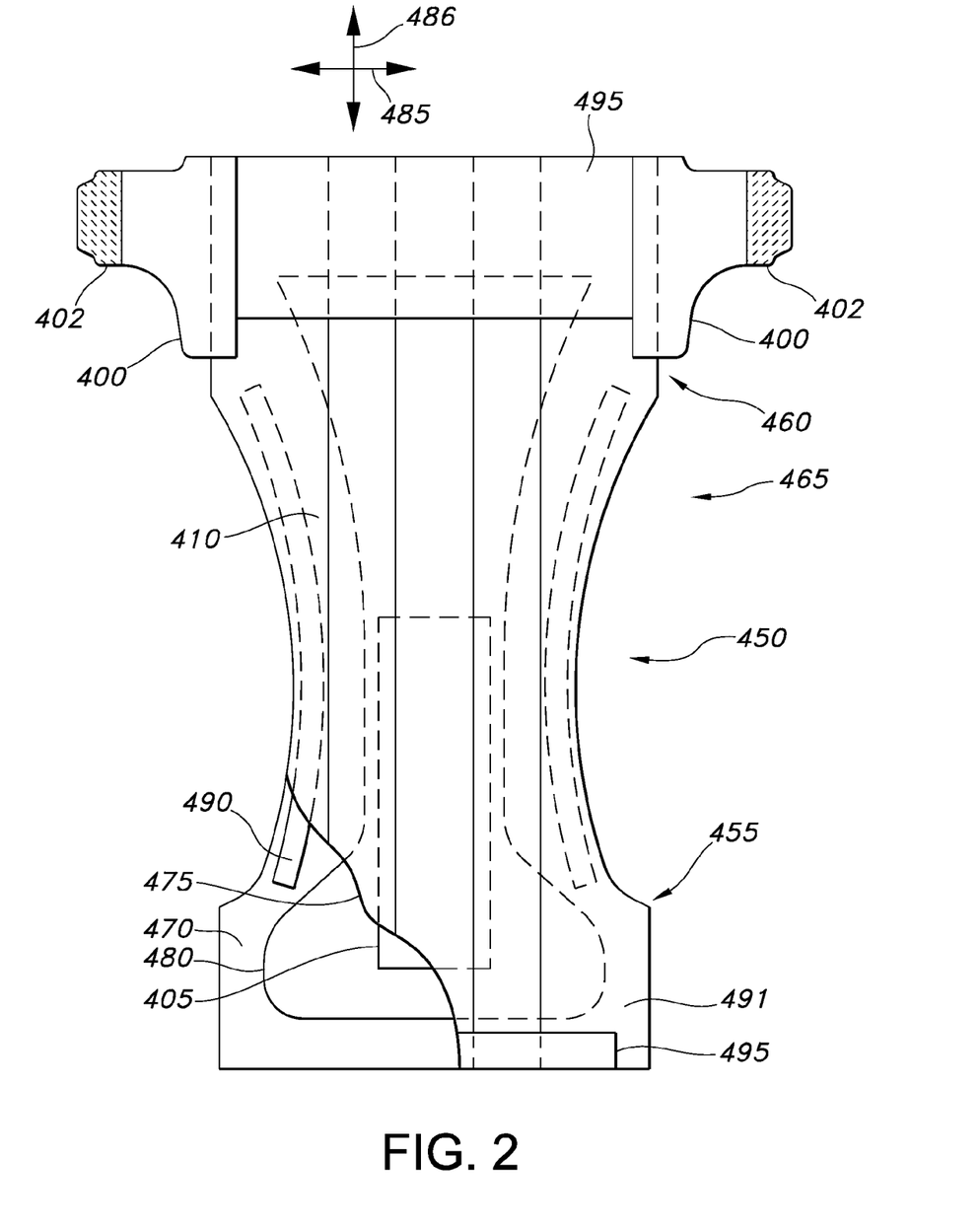
FIG. 2 is a bottom plan view similar to FIG. 1 showing the surface of the personal care product that faces the wearer when worn.

Referring to FIGS. 1 and 2, one embodiment of a disposable diaper 450 is shown that generally defines a front waist section 455, a rear waist section 460, and an intermediate section 465 that interconnects the front and rear waist sections. The front and rear waist sections 455 and 460 include the general portions of the diaper which are constructed to extend substantially over the wearer's front and rear abdominal regions, respectively, during use. The intermediate section 465 of the diaper includes the general portion of the diaper that is constructed to extend through the wearer's crotch region between the legs. Thus, the intermediate section 465 is an area where repeated liquid surges typically occur in the diaper. The diaper 450 has an inner (body-side) surface 491 which faces the wearer and an outer (garment-side) surface 492 which faces away from the wearer.

The diaper 450 includes, without limitation, an outer cover, or backsheet 470, a liquid permeable bodyside liner, or topsheet 475, positioned in facing relation with the backsheet 470, and an absorbent core body, or liquid retention structure, 480, such as an absorbent pad, which is located between the backsheet 470 and the topsheet 475. The backsheet 470 defines a length, or longitudinal direction 486, and a width, or lateral direction 485 which, in the illustrated embodiment, coincide with the length and width of the diaper 450. The liquid retention structure 480 generally has a length and width that are less than the length and width of the backsheet 470, respectively. Thus, marginal portions of the diaper 450, such as marginal sections of the backsheet 470 may extend past the terminal edges of the liquid retention structure 480. In the illustrated embodiments, for example, the backsheet 470 extends outwardly beyond the terminal marginal edges of the liquid retention structure 480 to form side margins and end margins of the diaper 450. The topsheet 475 is generally coextensive with the backsheet 470 but may optionally cover an area that is larger or smaller than the area of the backsheet 470, as desired.

The backsheet 470 is substantially liquid impermeable to inhibit body exudates against leaking from the diaper 450 and wetting articles, such as bed sheets and clothing, as well as the wearer and caregiver. The backsheet 470 may be constructed of a single layer of liquid impermeable material or more suitably it may be a multi-layered laminate structure in which at least one of the layers is liquid impermeable. For instance, the backsheet 470 can include a liquid permeable outer layer and a liquid impermeable inner layer joined together by a laminate adhesive, or by ultrasonic bonds, thermal bonds, or the like. In such a multi-layered embodiment, the inner layer of the backsheet 470 can be both liquid and vapor impermeable, or it may be liquid impermeable and vapor permeable (breathable). For example, the inner layer can be manufactured from a thin plastic film, although other flexible liquid impermeable materials may be used. For example, the breathable film may be a microporous or monolithic film.

Alternative constructions of the backsheet 470 may comprise a woven or non-woven fibrous web layer which has been totally or partially constructed or treated to impart the desired levels of liquid impermeability to selected regions that are adjacent or proximate the absorbent core body 480. For example, the outer cover may include a gas-permeable, non-woven fabric layer laminated to a polymer film layer which may or may not be gas-permeable (breathable). If desired, the film may be formed from a polyolefin polymer, such as linear, low-density polyethylene (LLDPE) or polypropylene. Examples of predominately linear polyolefin polymers include, without limitation, polymers produced from the following monomers: ethylene, propylene, 1-butene, 4-methylpentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers.

Other examples of fibrous, cloth-like backsheet materials can comprise a stretch thinned or stretch thermal laminate material. Examples of microporous films are described in U.S. Pat. No. 5,843,057 to McCormack; U.S. Pat. No. 5,855,999 to McCormack; U.S. Pat. No. 5,932,497 to Morman, et al.; U.S. Pat. No. 5,997,981 to McCormack et al.; U.S. Pat. No. 6,002,064 to Kobylivker, et al.; U.S. Pat. No. 6,015,764 to McCormack, et al.; U.S. Pat. No. 6,037,281 to Mathis, et al.; U.S. Pat. No. 6,111,163 to McCormack, et al.; and U.S. Pat. No. 6,461,457 to Taylor, et al., which are incorporated herein in their entirety by reference thereto for all purposes. Suitable techniques for bonding a film to a nonwoven web are described in U.S. Pat. No. 5,843,057 to McCormack; U.S. Pat. No. 5,855,999 to McCormack; U.S. Pat. No. 6,002,064 to Kobylivker, et al.; U.S. Pat. No. 6,037,281 to Mathis, et al.; and WO 99/12734, which are incorporated herein in their entirety by reference thereto for all purposes.

In some embodiments, the backsheet 470 may be stretchable, and in other embodiments the outer cover may be elastic. As used herein, the term "stretchable" refers to a material that may be extensible and/or elastic. That is, the material may be extended, deformed or the like, without breaking, and may or may not significantly retract after removal of an extending force. The terms "elastic" and "elastomeric" as used herein refer to a material which, upon application of an elongating force, is elongatable in at least one direction and retracts to dimensions close to its original dimensions (e.g., within at least about 25 percent) upon removal of the elongating force. For example, an elastic material elongated by an elongating force to a length which is at least 50 percent greater than the relaxed, unelongated length of the material will recover to within at least about 25 percent of its relaxed, unelongated length within a short period of time (e.g., about one minute) following removal of the elongating force. The term "extensible" refers to a material which, upon removal of an elongating force, experiences a substantially permanent deformation or the material does not exhibit a significant retractive force.

As an example, the backsheet 470 may be composed of a single layer, multiple layers, laminates, spunbond fabrics, films, meltblown fabrics, elastic netting, microporous web, bonded carded webs or foams comprised of elastomeric or polymeric materials. Elastomeric laminate webs may include an elastic non-woven material or film joined to one or more gatherable non-woven webs, films, or foams. Stretch bonded film or fiber laminates (SBL) and neck bonded laminates (NBL) are examples of elastomeric composites. Examples of suitable non-woven materials are spunbond-meltblown fabrics, spunbond-meltblown-spunbond fabrics, spunbond fabrics, or laminates of such fabrics with films, foams, or other non-woven webs.

Suitable elastomeric materials may include cast or blown films, foams, or meltblown fabrics composed of elastomeric polyethylene, polypropylene, polyolefin copolymers, elastomeric polyesters, elastomeric polyurethanes, elastomeric polyamides, as well as combinations thereof. The elastomeric materials may include PEBAX® elastomer (available from AtoChem located in Philadelphia, Pa.), HYTREL® elastomeric polyester (available from E.I. DuPont de Nemours located in Wilmington, Del.), KRATON® elastomer (available from Kraton Polymers of Houston, Tex.), SEPTON® elastomer available from Kuraray Company, Ltd. of Okayama, Japan, or strands of LYCRA® elastomer (available from E.I. DuPont de Nemours located in Wilmington, Del.), or the like, as well as combinations thereof. Examples of elastomeric polyolefins include ultra-low density elastomeric polypropylenes and polyethylenes, such as those produced by "single-site" or "metallocene" catalysis methods. Such elastomeric olefin polymers are commercially available from ExxonMobil Chemical Co. of Houston, Tex. under the trade designations ACHIEVE® (propylene-based), EXACT® (ethylene-based), and EXCEED® (ethylene-based). Elastomeric olefin polymers are also commercially available from DuPont Dow Elastomers, LLC (a joint venture between DuPont and the Dow Chemical Co.) under the trade designation ENGAGE® (ethylene-based) and AFFINITY® (ethylene-based).

The backsheet 470 may include materials that have elastomeric properties through a mechanical process, a printing process, a heating process, and/or a chemical treatment. For examples such materials may be apertured, creped, neck-stretched, heat activated, embossed, and micro-strained.

The topsheet 475 presents a body-facing surface 491 which isolates the wearer's skin from liquids retained by the absorbent core 480, and is suitably compliant, soft-feeling, and non-irritating to the wearer's skin. Further, the topsheet 475 can be less hydrophilic than the absorbent core 480, and is sufficiently porous to be liquid permeable, permitting liquid to readily penetrate through its thickness to reach the absorbent core. A suitable topsheet 475 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers.

Various woven, knitted and non-woven fabrics can be included in the topsheet 475. For example, the topsheet 475 may include a meltblown web, a spunbond web, or a bonded-carded-web composed of the desired fibers. The various fabrics can be composed of natural fibers, synthetic fibers or combinations thereof. In particular aspects, the topsheet 475 may be comprised of polymer fibers, networks, laminates, liquid permeable films, cellulosic fibers, rayon, water swellable gels, and elastomeric materials, as well as combinations thereof. Suitable materials for the topsheet 475 can include meltblown webs, airlaid webs, spunbond webs, or bonded-carded webs of synthetic continuous or discrete polymer fibers and/or natural fibers, a pattern bonded spunbonded web, airlaid web, or bonded carded web, as well as combinations thereof. Suitable polymers can include polypropylene, polyethylene, polyester, nylon and bicomponent and biconstituent materials composed of these polymers. In some embodiments, the topsheet 475 can be stretchable, and in other embodiments the topsheet may be elastic, in which the topsheet may include elastomeric components such as described above for the backsheet 470.

The topsheet 475 may be composed of a substantially hydrophobic material, and the hydrophobic material may optionally be treated with a surfactant or otherwise processed to impart a desired level of wettability and hydrophilicity. For example, in one embodiment the topsheet 475 can be a non-woven, spunbond polypropylene fabric which is surface treated with an operative amount of surfactant, such as about 0.45% AHCOVEL® Base N62 surfactant, available from Uniqema, a division of ICI, a business having offices located in New Castle, Del. The surfactant can be applied by any conventional means, such as spraying, printing, brush coating or the like.

To provide improved fit and to help reduce leakage of body exudates from the diaper 450, the diaper side margins and end margins may be elasticized with suitable elastic members, as further explained below. For example, as representatively illustrated in FIG. 1, the diaper 450 may include leg elastics 490 constructed to operably tension the side margins of the diaper 450 to provide elasticized leg bands which can closely fit around the legs of the wearer to reduce leakage and provide improved comfort and appearance. Waist elastics 495 are employed to elasticize the end margins of the diaper 450 to provide elasticized waistbands. The waist elastics 495 are configured to provide a resilient, comfortably close fit around the waist of the wearer. Suitable, the waist elastics may include elastic materials such as described above for the backsheet. Exemplary of such materials are laminate sheets that either comprise or are adhered to the backsheet, such that elastic constrictive forces are imparted to the backsheet 470.

As is known, fastening means, such as hook and loop fasteners, may be employed to secure the diaper 450 on a wearer. Alternatively, other fastening means, such as buttons, pins, snaps, adhesive tape fasteners, cohesives, fabric-and-loop fasteners, or the like, may be employed. In the illustrated embodiment, the diaper 450 includes a pair of side panels 400 (or ears) to which the fasteners 402, indicated as the hook portion of a hook and loop fastener, are attached. Generally, the side panels 400 are attached to the side edges of the diaper in one of the waist sections 455, 460 and extend laterally outward therefrom. The side panels 400 may be elasticized or otherwise rendered elastomeric by use of an elastic composite capable of stretching in a direction generally parallel to the transverse/lateral axis of the diaper. In particular embodiments, suitable elastic materials from which the side panels 400 may be constructed may include a stretch-thermal laminate (STL), a neck-bonded laminate (NBL), a reversibly necked laminate, or a stretch-bonded laminate (SBL) material. The elastic materials from which the side panels 400 may be constructed may include elastic polymers such as described above for elastic backsheet materials. Methods of making such materials are well known to those skilled in the art and described in U.S. Pat. No. 4,663,220 to Wisneski et al.; U.S. Pat. No. 4,720,415 to Taylor et al.; U.S. Pat. No. 5,226, 992 to Morman; and U.S. Pat. No. 6,969,441 to Welch et al.; all of which are incorporated herein by reference. Alternatively, the side panel material may comprise other suitable woven or non-woven materials. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

The diaper 450 may also include a surge management layer 405, located between the topsheet 475 and the liquid retention structure 480, to rapidly accept fluid exudates and distribute the fluid exudates to the liquid retention structure 480 within the diaper 450. The diaper 450 may further include a ventilation layer (not illustrated), also called a spacer, or spacer layer, located between the liquid retention structure 480 and the backsheet 470 to insulate the backsheet 470 from the liquid retention structure 480 to reduce the dampness of the garment at the exterior surface of a breathable outer cover, or backsheet, 470. Examples of suitable surge management layers 405 are described in U.S. Pat. No. 5,486,166 to Bishop and U.S. Pat. No. 5,490,846 to Ellis.

The disposable diaper 450 may also include a pair of containment flaps 410 which are configured to provide a barrier to the lateral flow of body exudates. The containment flaps 410 may be located along the laterally opposed side edges of the diaper adjacent the side edges of the liquid retention structure 480. Each containment flap 410 typically defines an unattached edge that is configured to maintain an upright, perpendicular configuration in at least the intermediate section 465 of the diaper 450 to form a seal against the wearer's body. The containment flaps 410 may extend longitudinally along the entire length of the liquid retention structure 480 or may only extend partially along the length of the liquid retention structure. When the containment flaps 410 are shorter in length than the liquid retention structure 480, the containment flaps 410 can be selectively positioned anywhere along the side edges of the diaper 450 in the intermediate section 465. Such containment flaps 410 are generally well known to those skilled in the art.

For example, suitable constructions and arrangements for containment flaps 410 are described in U.S. Pat. No. 4,704,116 to Enloe.

The diaper 450 may also include one or more areas of heat-activatable expandable treatment 420. The areas of heat-activatable expandable treatment 420 provide visible and tactile cues on the various surfaces of the diaper 450. Visible cues are provided to a user or caregiver when the heat-activatable expandable treatment 420 has a color distinct from the color of the surrounding surface. Tactile cues are provided to a user or caregiver because the areas of heat-activatable expandable treatment 420 are raised above the surrounding surface and thus detectable to the touch. In some embodiments, the areas of heat-activatable expandable treatment 420 may be on the garment-facing surface 492 of the backsheet 470. In other embodiments, the areas of heat-activatable expandable treatment 420 may be on the body-facing surfaces 491 of the topsheet 475 or the side panels 400.

The heat-activatable expandable treatment 420 may be applied in any suitable shape or pattern. Suitably, the shape or pattern will provide some visible cue to a user or caregiver.

In some embodiments, the heat-activatable expandable treatment 420 may be on the surface of a suitable nonwoven material. Suitable nonwoven materials include those described above for backsheet, liner, and side panels, such as, for example, film nonwoven laminates, stretch-thinned laminates, stretch-bonded laminates, and neck-bonded laminates.

The areas of heat-activatable expandable treatment 420 may provide improved surface properties when applied to a visible outer surface of the diaper 470. For example, grip zones 425 applied to the garment-facing surface (shown) or the body-facing surface (not shown) of the side panels 400 provide improved grippability. By "grippability" it is meant that the side panels 400 are more readily grasped and held during the process of pulling the side panels around the waist of the wearer. In some embodiments, the heat-activatable expandable treatment 420 forms a rubbery, compressible surface that improves grippability. In other embodiments, the heat-activatable expandable treatment 420 may increase the stiffness of the side panel 400, thus making the side panel more resistant to surface deformation or bunching. The grip zones 425 are shown in the shape of fingerprints to provide an intuitive cue to a user as to where to most effectively grasp the product during handling and placement of the product, however, any suitable shape or pattern suggestive of a grip zone may be used.

In some embodiments, the areas of heat-activatable expandable treatment may be applied near the front or rear waist areas 455, 460. In one embodiment, the area of heat-activatable expandable treatment 420 is applied as a series of spaced lines 430. The spaced lines 430 visually identify the area of the diaper 450 where gathers of an elastic waistband may be present, whether or not an elastic waistband is actually present. The spaced lines 430 provide a tactile cue that an elastic waistband may be present as a user or caregiver runs his/her fingers across the surface of the product, thus reinforcing the visual cue provided by the spaced lines. Suitably, the product would be stretchable in the area of heat-activatable expandable treatment. The spaced lines 430 would be able to separate as the product is stretched in the area of heat-activatable expandable treatment, thus further reinforcing the notion that an elastic waist band may be present, whether or not an elastic waistband is actually present.

In another embodiment, the area of heat-activatable expandable treatment 420 is applied on the rear waist area 460 in the shape of a product tag or label 435. As a product tag is often associated with the back of a product, placement of the area of heat-activatable expandable treatment 420 as a product tag 435 will further differentiate the rear of the product from the front of the product in both a visual and tactile way, thus making it easier for a caregiver of user to don the product properly.

Suitable materials for the heat-activatable expandable treatment 420 include heat-activatable expandable inks, such as Aqua Puff inks obtainable from Polytex Environmental inks. Aqua Puff inks are expandable inks which react when exposed to heat to produce a gas by-product that causes the ink to expand or "puff up". Suitable Aqua Puff inks include Puff Ink MW 4319 and MW 4404.

In some aspects, the heat-activatable expandable treatment 420 can include an optional elastomeric polymer. The elastomeric polymer may add resilience or flexibility to the heat-activatable expandable treatment. The elastomeric polymer component should be present in an amount which is effective to achieve the desired dimensional change properties and the desired tactile properties. The elastomeric polymer can be present in an amount as desired, provided that it does not diminish the effectiveness of the heat-activatable expandable treatment. For example, in some aspects, the heat-activatable expandable treatment can contain up to about 1 wt %, such as up to about 5 wt %, or even up to about 10 wt % or more elastomeric polymer to provide improved benefits. Examples of suitable elastomeric polymers include, but are not limited to, thermoplastic polyurethanes, poly(ether-amide) block copolymers, thermoplastic rubbers such as uncrosslinked polyolefins, styrene-butadiene copolymers, silicon rubbers, synthetic rubbers such as nitrile rubber, styrene isoprene copolymers, styrene ethylene butylenes copolymers, butyl rubber, nylon copolymers, spandex fibers comprising segmented polyurethane, ethylene-vinyl acetate copolymer or mixtures thereof.

Additionally, adhesion promoters can be added to the heat-activatable expandable treatment. For example, Carboset 514H, available commercially from Noveon, Inc. of Cleveland, Ohio, is an acrylic colloidal dispersion polymer supplied in ammonia water, which can dry to a clear, water-resistant, non-tacky thermoplastic polymer.

In addition, the heat-activatable expandable treatment 420 can generally contain a coloring agent (e.g., pigment or dye), a solvent, and any other desired ingredients. Typically, a pigment refers to a colorant based on inorganic or organic particles which do not dissolve in water or solvents. Usually pigments form an emulsion or a suspension in water. On the other hand, a dye generally refers to a colorant that is soluble in water or solvents.

The pigment or dye in the heat-activatable expandable treatment 420 can be present in an amount effective to be visible once applied to the substrate. For example, the pigment or dye can be present in the ink composition at concentration between about 0.25% to about 40% based on the dry weight basis, and preferably between greater than or equal to about 1% and less than or equal to about 10%.

Suitable organic pigments, include dairylide yellow AAOT (for example, Pigment Yellow 14 CI No. 21 095), dairylide yellow AAOA (for example, Pigment Yellow 12 CI No. 21090), Hansa Yellow, CI Pigment Yellow 74, Phthalocyanine Blue (for example, Pigment Blue 15), lithol red (for example, Pigment Red 52:1 CI No. 15860: 1). toluidine red (for example. Pigment Red 22 CI No. 12315), dioxazine violet (for example, Pigment Violet 23 CI No. 51319), phthalocyanine green (for example, Pigment Green 7 CI No. 74260), phthalocyanine blue (for example, Pigment Blue 15 CI No. 74160), naphthoic acid red (for example, Pigment Red 48:2 CI No. 15865:2). Inorganic pigments include titanium dioxide (for example, Pigment White 6 CI No. 77891), carbon black (for example, Pigment Black 7 CI No. 77266), iron oxides (for example, red, yellow. and brown), ferric oxide black (for example, Pigment Black 11 CI No. 77499), chromium oxide (for example, green), ferric ammonium ferrocyanide (for example, blue), and the like.

Suitable dyes that may be used include, for instance, acid dyes, and sulfonated dyes including direct dyes. Other suitable dyes include azo dyes (e.g., Solvent Yellow 14, Dispersed Yellow 23, and Metanil Yellow), anthraquinone dyes (e.g., Solvent Red 111, Dispersed Violet 1, Solvent Blue 56, and Solvent Orange 3), xanthene dyes (e.g., Solvent Green 4, Acid Red 52, Basic Red 1, and Solvent Orange 63), azine dyes (e.g., Jet Black), and the like.

The heat-activatable expandable treatment 420 is generally dispersed or dissolved in a low viscosity carrier. Water or other solvents may be used. Exemplary solvents are aliphatic hydrocarbons with common binder types, such as polyamide, shellac, nitro-cellulose, and styrene-maleic. Generally, solvent-based treatments include non-catalytic, block urethane resin, which generally demonstrate superior durability over traditional flexographic binders, such as styrene-maleic, rosin-maleic, and acrylic solutions. Desired solvent blends include various acetates such as ethyl acetate, N-propyl acetate, isopropyl acetate, isobutyl acetate, N-butyl acetate, and blends thereof; various alcohols including ethyl alcohol, isopropyl alcohol, normal propyl alcohol, and blends thereof; and glycol ethers including Ektasolve® EP (ethylene glycol monopropyl ether), EB (ethylene glycol monobutyl ether), DM (diethylene glycol monomethyl ether), DP (diethylene glycol monopropyl ether), and PM (propylene glycol monomethyl ether), which may be obtained from Eastman Chemical of Kingsport, Tenn. Other glycols that may also be used are DOWANOL® obtainable from Dow Chemical of Midland, Mich. A desired solvent blend may be a blend of about 50 percent to about 75 percent glycol ether, about 25 percent to about 35 percent N-propyl acetate, and about 15 percent to about 25 percent N-butyl acetate.

Suitable water-based heat-activatable expandable treatments 420 that may be used may further include emulsions that may be stabilized in water-ammonia and may further comprise alcohols, glycols, or glycol ethers as co-solvents. Generally, organic solvents (less than or equal to about 7 percent) may be added to water-based treatments: alcohols, for example, propan-2-ol may be added for speeding up drying and assisting wetting, glycols, for example, mono propylene glycol to slow down drying, glycol ethers, for example, dipropyl glycol mono methyl ether to aid film formation. Such solvents may be commodity chemicals, commercially available from various companies. Generally, water-based treatments include self-crosslinking acrylic copolymer emulsion, which may have demonstrated superior durability over traditional non-crosslinking binders such as acrylic solutions and dispersion copolymers. Besides the solvent and pigments, the heat-activatable expandable treatment may comprise a binder or mixtures thereof. The binder helps stabilize the heat-activatable expandable treatment onto the applicable surface of the product. Generally, the pigment-to-binder ratio is typically from 1:20 to 1:2.

Waxes may also be included in the heat-activatable expandable treatment 420 to increase the slip and improve the rub-resistance of the heat-activatable expandable treatment. Common classifications of waxes include animal (for example, beeswax and lanolin), vegetable (for example, carnauba and candellilia), mineral (for example, paraffin and microcrystalline), and synthetic (for example. Polyethylene, polyethylene glycol, and Teflon®). In one embodiment, a wax can be present in an amount of about 0.5 percent to about 5 percent based on the total heat-activatable expandable treatment formulation weight when wet.

In one embodiment, the heat-activatable expandable treatment 420 used may contain particulates. For example, the heat-activatable expandable treatment may contain activated carbon particles and the like. Activated carbon particles are useful for absorbing odors that may be associated with use of personal care products.

The heat-activatable expandable treatment chosen should, of course, be safe for human use and should not have environmentally deleterious effects. Moreover, it is desirable that the heat-activatable expandable treatment composition is suitable for the intended application process and is preferably temperature resistant to the process employed for forming the absorbent article, e.g., the temperatures used during a vacuum aperturing process and the like elevated heating processes.

Additional (or multiple) heat-activatable expandable treatments may be applied to the substrate material. Each treatment may comprise the same material, or they can comprise different materials. As the heat-activatable expandable inks are available in a variety of colors, in some aspects the inks may be used to additionally provide a visually distinctive multi-color appearance to the product. Use of combinations of colors and patterns can create visual cues that provide different signals to a user, for example, degrees of protection, comfort, and/or effectiveness, and so forth. Changes to these patterns and colors could be as easy as changing the ink and printing plate, which are much more economical and quicker than other methods of patterning, e.g., embossing. Alternatively, various patterns and colors may be used to accentuate other elements on the product, e.g., embossing patterns.

The heat-activatable expandable treatment 420 may be applied to a substrate, product component, or product by any particular treatment application method. Exemplary treatment methods include printing, including, but not limited to flexography, gravure, offset, inkjet (digital), silk screen, rotary screen printing, and so forth, spraying, dipping and squeezing, curtain coating, knife and roll coating, and other techniques as are well known in the art. The application method can be used to create any design, figure, or other image on the surface of the product. The application of the heat-activatable expandable treatment can occur at a number of steps in the converting process, such as on an off-line printing step, or on-line during the product assembly process. Further, the heat-activatable expandable treatment can be applied at one process step, and expanded by heat activation at a downstream step. It is believed that a more efficient process may be achieved by not linking the printing step with the heat-activation step.

The heat-activatable expandable treatment can be applied directly to a surface, without any other layer or coating positioned between the surface and the heat-activatable expandable treatment. However, if desired, a treatment composition can be applied to the surface prior to application of the heat-activatable expandable treatment to further adhere the heat-activatable expandable treatment to the surface. Exemplary treatment compositions that can be utilized are disclosed in U.S. Publication No. 2004/0121675 of Snowden, et al., U.S. Publication No. 2006/0003150 to Braverman, et al., and U.S. Publication No. 2006/0246263 to Yahiaoui, et al., all of which are herein incorporated by reference.

The heat-activatable expandable treatment is capable of being activated upon application of sufficient heat to the heat-activatable expandable treatment. The heat-activatable expandable treatment, upon exposure to heat, will expand, grow in size, or "puff up". Application of the heat may occur by any suitable means, such as for example, treatment with a hot air stream, passing through a heat tunnel, contact with a hot surface, e.g. a steam can, iron, and so forth, treatment with infrared radiation, treatment with microwaves, and so forth.

When heat is applied to the heat-activatable expandable treatment, the heat-activatable expandable treatment will expand in volume, rising a distance from the surface of the substrate. The distance will vary as desired. For example, the distance that a given heat-activatable expandable treatment will expand can be at least about 0.1 millimeter (mm), such as at least about 0.5 mm, or at least about 1 mm or more to provide improved benefits. As further examples, the heat-activatable expandable treatment may expand from about 0.1 mm to about 10 mm, or from about 0.2 mm to about 6 mm, or from about 0.5 mm to about 5 mm. The distance of expansion can be modified as desired according to several factors, including the expanding ability of the heat-activatable treatment, the temperature reached, and the amount of time the material is heated and so forth. In one aspect, different heat-activatable expandable treatments in the product may be constructed of different heat-activatable expandable materials to create heat-activatable expandable treatments of varying height. For example, the height or thickness of the heat activatable expandable treatment can be greater than about 0.1 millimeter (mm), such as greater than about 0.5 mm, or greater than about 1 mm or more to provide improved benefits. As further examples, the heat-activatable expandable treatment may have a height or thickness from about 0.1 mm to about 10 mm, or from about 0.2 mm to about 6 mm, or from about 0.5 mm to about 6 mm.

Suitably, the heat-activatable expandable treatments are expanded by heating the treatments to a temperature greater than about 100° F., or greater than about 140° F. or greater than about 180° F. As further examples, the heat-activatable expandable treatments are expanded by heating the treatments to a temperature from about 100° F. to about 350° F., or from about 140° F. to about 330° F., or from about 180° F. to about 300° F.

Suitably, the heat-activatable expandable treatments are expanded by maintaining the treatments at the desired temperature for a period of time greater than about 0.5 seconds, or greater than about 1.0 seconds, or greater than about 1.5 seconds. As further examples, the heat activatable expandable treatments are expanded by maintaining the treatments at the desired temperature for a period of time from about 0.5 seconds to about 20 seconds, or from about 1.0 seconds to about 10 seconds, or from about 1.5 seconds to about 8 seconds.

The diaper 450 may be of various suitable shapes. For example, the diaper may have an overall rectangular shape, T-shape or an approximately hour-glass shape. In the shown embodiment, the diaper 450 has a generally I-shape. Other suitable components which may be incorporated on absorbent articles of the present invention may include waist flaps and the like which are generally known to those skilled in the art. Examples of diaper configurations suitable for use in connection with the elastic composite of the present invention that may include other components suitable for use on diapers are described in U.S. Pat. No. 4,798,603 to Meyer et al.; U.S. Pat. No. 5,176,668 to Bernardin; U.S. Pat. No. 5,176,672 to Bruemmer et al.; U.S. Pat. No. 5,192,606 to Proxmire et al.; and U.S. Pat. No. 5,509,915 to Hanson et al., which are incorporated herein in their entirety by reference thereto for all purposes.

One way to make these products more appealing is to print in bright colors on the products. Any desired design or other image can be applied or printed on an outer visible surface of a component using the heat-activatable expandable treatment disclosed herein. For example, a number of intricate, registered images can be printed on the outer visible surface of the backsheet 470. By outer "visible" surface is meant that surface of the product that is visible when the product is worn (i.e., the exposed outer surface of the absorbent article). Desirably, the designs can resist fading on the outercover, as well as preventing staining of anything (e.g., skin) that contacts the outercover.

The various regions and/or components of the diaper 450 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the topsheet 475 and backsheet 470 may be assembled to each other and to the liquid retention structure 480 with lines of adhesive, such as a hot melt, pressure-sensitive adhesive. Similarly, other diaper components, such as the elastic members 490 and 495, fastening members 402, and surge layer 405 may be assembled into the article by employing the above-identified attachment mechanisms.

Although various configurations of a diaper have been described above, it should be understood that other diaper and absorbent article configurations are also included within the scope of the present invention. In addition, the present invention is by no means limited to diapers. In fact, several examples of absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Further, other examples of personal care products that may incorporate such materials are training pants (such as in side panel materials) and feminine care products. By way of illustration only, training pants suitable for use with the present invention and various materials and methods for constructing the training pants are disclosed in U.S. Pat. No. 6,761,711 to Fletcher et al.; U.S. Pat. No. 4,940,464 to Van Gompel et al.; U.S. Pat. No. 5,766,389 to Brandon et al.; and U.S. Pat. No. 6,645,190 to Olson et al., which are incorporated herein in their entirety by reference thereto for all purposes.

These and other modifications and variations to the present invention may be practiced by those of ordinary skill in the art, without departing from the spirit and scope of the present invention, which is more particularly set forth in the appended claims. In addition, it should be understood that the aspects of the various embodiments may be interchanged either in whole or in part. Furthermore, those of ordinary skill in the art will appreciate that the foregoing description is by way of example only, and is not intended to limit the invention so further described in the appended claims.

The invention claimed is:

1. An absorbent article comprising:
   a. a topsheet, which forms a body-facing surface of the absorbent article;
   b. a backsheet disposed distally from the topsheet, which forms a garment-facing surface of the absorbent article; and
   c. an absorbent core positioned between the topsheet and the backsheet; and
   d. a heat-activatable expandable treatment printed directly on the garment-facing surface;
      wherein the heat-activatable expandable treatment comprises activated carbon particles.

2. The absorbent article of claim 1 wherein the garment-facing surface is on a nonwoven material.

3. The absorbent article of claim 2 wherein the nonwoven material is selected from the group consisting of film/nonwoven laminates, stretch-thinned laminates, stretch-bonded laminates and neck-bonded laminates.

4. The absorbent article of claim 1 wherein the heat-activatable expandable treatment has a thickness above the garment-facing surface of between about 0.2 and about 6 millimeters.

5. The absorbent article of claim 1 wherein the garment-facing surface has a first color and the heat-activatable expandable treatment has a second color different than the first color.

6. The absorbent article of claim 1 wherein the heat-activatable expandable treatment is on the garment-facing surface in a visually distinctive shape or pattern.

7. The absorbent article of claim 6 wherein the heat-activatable expandable treatment is in a series of spaced lines, the lines spaced substantially in a stretch direction of the backsheet.

8. The absorbent article of claim 7 wherein the stretch direction of the backsheet corresponds to a lateral direction of the backsheet.

9. The absorbent article of claim 1 wherein the heat-activatable expandable treatment is on the garment-facing surface in a visually distinctive shape or pattern indicating where the garment-facing surface should be grasped during donning of the article.

10. The absorbent article of claim 1 wherein the heat-activatable expandable treatment is in the area of a waistband or a fastener.

11. The absorbent article of claim 1 wherein the heat-activatable expandable treatment is on a rear waist region of the absorbent article and in a shape of a product label.

12. The absorbent article of claim 1 wherein the absorbent article is a diaper, a training pant, a swimming pant, or a feminine care article.

13. An absorbent article comprising:
  a. a topsheet, which forms a body-facing surface of the absorbent article;
  b. a backsheet disposed distally from the topsheet, which forms a garment-facing surface of the absorbent article; and
  c. an absorbent core positioned between the topsheet and the backsheet; and
  d. a heat-activatable expandable treatment printed directly on the garment-facing surface;
    wherein the heat-activatable expandable treatment comprises an elastomeric polymer.

14. A method of preparing an absorbent article comprising the steps of providing an absorbent article comprising:
  a. a topsheet which forms a body-facing surface of the absorbent article;
  b. a backsheet disposed distally from the topsheet which forms a garment-facing surface of the absorbent article; and
  c. an absorbent core positioned between the topsheet and the backsheet;
    applying a heat-activatable expandable treatment by printing directly onto the garment-facing surface; and,
    heating the heat-activatable expandable treatment to expand the heat-activatable expandable treatment;
    wherein the heat-activatable expandable treatment comprises an elastomeric polymer.

15. The method of preparing an absorbent article of claim 14 wherein the heating step comprises heating the heat-activatable expandable treatment to a temperature greater than about 100 degrees Fahrenheit.

16. The method of preparing an absorbent article of claim 14 wherein the heat-activatable expandable treatment has a thickness of between about 0.2 and about 6 millimeters after the heating step.

17. The method of preparing an absorbent article of claim 14 wherein the garment-facing surface has a first color and the heat-activatable expandable treatment has a second color different than the first color.

18. The method of preparing an absorbent article of claim 14 wherein the backsheet comprises a nonwoven material.

19. The method of preparing an absorbent article of claim 14 wherein the heat-activatable expandable treatment is applied to the garment-facing surface in a visually distinctive shape or pattern.

20. The method of preparing an absorbent article of claim 19 wherein the heat-activatable expandable treatment is applied to the garment-facing surface as a series of spaced lines in a waist region of the absorbent article, the lines spaced substantially in a stretch direction of the waist region.

21. The method of preparing an absorbent article of claim 20 wherein the stretch direction of the waist region corresponds to a lateral direction of the backsheet.

22. The method of preparing an absorbent article of claim 14 wherein the heat-activatable expandable treatment is applied in a visually distinctive shape or pattern indicating where the absorbent article should be grasped during donning of the article.

23. The method of preparing an absorbent article of claim 14 wherein the heat-activatable expandable treatment is in the area of a waistband or a fastener.

24. The method of preparing an absorbent article of claim 14 wherein the heat-activatable expandable treatment is applied to the garment-facing surface either before or after assembly of the absorbent article.

25. The method of preparing an absorbent article of claim 14 wherein the heating step occurs either before or after assembly of the absorbent article.

26. A method of preparing an absorbent article comprising the steps of providing an absorbent article comprising:
  a. a topsheet which forms a body-facing surface of the absorbent article;
  b. a backsheet disposed distally from the topsheet which forms a garment-facing surface of the absorbent article; and
  c. an absorbent core positioned between the topsheet and the backsheet;
    applying a heat-activatable expandable treatment by printing directly onto the garment facing surface; and,
    heating the heat-activatable expandable treatment to expand the heat-activatable expandable treatment;
    wherein the heat-activatable expandable treatment comprises activated carbon particles.

\* \* \* \* \*